US008088939B2

(12) United States Patent
Strickler et al.

(10) Patent No.: US 8,088,939 B2
(45) Date of Patent: Jan. 3, 2012

(54) PROCESSES FOR PRODUCING TRANSITION METAL AMIDES

(75) Inventors: Jamie R. Strickler, Baton Rouge, LA (US); Feng-Jung Wu, Baton Rouge, LA (US)

(73) Assignee: Albemarle Corporation, Baton Rouge, LA (US)

( * ) Notice: Subject to any disclaimer, the term of this patent is extended or adjusted under 35 U.S.C. 154(b) by 143 days.

(21) Appl. No.: 12/676,289

(22) PCT Filed: Sep. 5, 2008

(86) PCT No.: PCT/US2008/075317
§ 371 (c)(1), (2), (4) Date: Mar. 3, 2010

(87) PCT Pub. No.: WO2009/032970
PCT Pub. Date: Mar. 12, 2009

(65) Prior Publication Data

US 2010/0204499 A1 Aug. 12, 2010

Related U.S. Application Data

(60) Provisional application No. 60/970,352, filed on Sep. 6, 2007.

(51) Int. Cl.
*C07F 9/00* (2006.01)
*C07F 15/00* (2006.01)
*C07F 7/00* (2006.01)

(52) U.S. Cl. ............ 556/42; 556/51; 556/136; 556/138; 534/15

(58) Field of Classification Search .................... 556/42, 556/51, 136, 138; 534/15
See application file for complete search history.

(56) References Cited

U.S. PATENT DOCUMENTS

| | | | |
|---|---|---|---|
| 6,552,209 | B1 | 4/2003 | Lei et al. |
| 6,831,188 | B1 | 12/2004 | Beard et al. |

OTHER PUBLICATIONS

XP009025082; D. C. Bradley, et al; "Metallo-Organic Compounds Containing Metal-Nitrogen Bonds. Part I. Some Dialkylamino-Derivatives of Titanium and Zirconium"; Journal of the Chemical Society; 1960; pp. 3857-3861.

Robert E. Blake, Jr., et al; "A Cationic Imido Complex of Permethyltantalocene: H2 and Carbon-Hydrogen Bond Activation, [2+2] Cycloaddition Reactions, and an unusual Reaction With Carbon Dioxide That Affords Coordinated Isocyanate"; Organometallics; 1998; vol. 17; pp. 718-725.

Christopher C. Cummins, et al; "(Tri-tert-butylsilyl)imido Complexes of Titanium: Benzene C-H Activation and Structure of [(tBu3SiNH)Ti]2(μ-NSitBu3)2"; Journal of the American Chemical Society; 1991; vol. 113; No. 8; pp. 2985-2994.

Carlos F. Barrientos-Penna, et al; "Aryldiazenido, Aryldiazene, and Arylhydrazido Complexes: Derivatives of Dicarbonyl(η5-cyclopentadienyl)rhenium and the X-Ray Structure of [(n5-C5H5)Re(CO)2[p-NN(CH3)C6H4OMe]]"; Inorganic Chemistry; 1982; vol. 21; No. 7; pp. 2578-2585.

Richard R. Schrock, et al; "Synthesis of Zirconium Complexes That Contain the Diamidophosphine Ligands [(Me3SiNCH2CH2)2PPh]2- Or [(RNSiMe2CH2)2PPh]2- (R=t-Bu or 2,6-Me2C6H3)"; Organometallics; 1999; vol. 18; No. 3; pp. 428-437.

Andrew D. Garrett, et al; "Reactivity Relationships Between Chiral Cyclic Amido and Imine Tungsten(II) Complexes"; Organometallics; 2006; vol. 25; No. 7; pp. 1728-1734.

Andreas A. Danopoulos, et al; "Dilithium Tetra(t-butylimido)-molybciate(VI) and -tungstate(VI) and Some Reactions Thereof. X-Ray Cystal Structures of W[(μ-NBut)2AIX2]2(X=Cl or Me), [W(NBut)2(NH2But)Cl(μ-Cl)]2, and [W2Cu5(NBut)2(μ-NBut)6(NHBut)2]BF4"; Journal of the Chemical Society, Dalton Transactions; 1990; pp. 2753-2761.

Andreas A. Danopoulos, et al; "Imido Analogues of the Tungstate(VI) and Perrhenate(VII) Ions. X-ray Crystal Structures of Li2W(NBut)4 and Li(tmed)Re(NBut)4"; Journal of the Chemical Society, Chemical Communications; 1989; pp. 896-897.

Andreas A. Danopoulos, et al; "Imido Complexes of Molybdenum and Tungsten(VI); X-Ray Crystal Structure of cis-(η1-CF3SO3)2W(NBut)2(NH2But)2"; Polyhedron; 1989; vol. 8; No. 24; pp. 2947-2949.

Gary M. Diamond, et al; "Synthesis of Group 4 Metal rac-(EBI)M(NR2)2 Complexes by Amine Elimination. Scope and Limitations"; Organometallics; 1996; vol. 15; No. 19; pp. 4030-4037.

Malcolm H. Chisholm, et al; "Tetrakisdimethylamidozirconium and Its Dimethylamido Lithium Adduct: Structures of [Zr(NMe2)4]2 and Zr(NMe2)6Li2(ThF)2"; Polyhedron; 1988; vol. 7; No. 24; pp. 2515-2520.

Gary M. Diamond, et al; "Efficient Synthesis of rac-(Ethylenebis(indenyl))ZrX2 Complexes Via Amine Elimination"; Organometallics; 1995; vol. 14; No. 1; pp. 5-7.

Hsin-Tien Chiu, et al; "Syntheses and Characterization of Organoimido Complexes of Tantalum; Potential Single-Source Precursors to Tantalum Nitride"; Polyhedron; 1998; vol. 17; Nos. 13-14; pp. 2187-2190.

William A. Nugent; "Synthesis of Some d0 Organoimido Complexes of the Early Transition Metals"; Inorganic Chemistry; 1983; vol. 22; No. 6; pp. 965-969.

*Primary Examiner* — Porfirio Nazario Gonzalez
(74) *Attorney, Agent, or Firm* — James A. Jubinsky

(57) ABSTRACT

Processes are provided for producing transition metal amides. In methods according to this invention, at least a halogenated transition metal and an amine are combined in a solvent to produce an intermediate composition and an alkylated metal or a Grignard reagent is added to the intermediate composition to produce the transition metal amide.

8 Claims, No Drawings

PROCESSES FOR PRODUCING TRANSITION METAL AMIDES

BACKGROUND

Metal amides are useful as precursor compounds for chemical vapor deposition; see, e.g., U.S. Pat. Nos. 5,178,911; 5,417,823; and 6,080,446. Metal amides are also useful in the synthesis of polymerization catalysts; see, e.g., U.S. Pat. No. 6,020,444. Metal amides are also useful in formation of metal-rich layers on materials having high dielectric constants, such as are used in construction of microelectronic devices; see, e.g., WO 02/27063.

Known processes for making metal amides require the transfer of a solid transition metal salt to a slurry of a lithium alkylamide. See, e.g., D. C. Bradley and I. M. Thomas, J. Chem. Soc., 1960, 3857-3861. The addition of solids into a reaction vessel with a reactive reagent present is a difficult and potentially hazardous operation on commercial scale since the flow is hard to control. The reverse reaction (i.e., adding a lithium amide to a metal halide slurry) is also possible, however the lithium amide salts are usually of low solubility and slurries of these salts tend to be nonhomogeneous, thick and difficult to completely transfer, and thus reaction stoichiometry cannot be adequately controlled to provide metal amides of commercially acceptable quality and quantity.

Accordingly, there is a need for improved synthetic routes for metal amides.

THE INVENTION

This invention meets the above-described need by providing methods of producing a metal amide comprising combining at least a halogenated transition metal and an amine composition in a solvent to produce an intermediate composition and combining at least (i) a portion of the intermediate composition and (ii) an alkylated metal or a Grignard reagent to produce at least the transition metal amide, wherein the amine composition comprises a primary amine, a secondary amine, or a diamine. An amine composition comprising a primary amine, a secondary amine, or a diamine, includes mixtures of two or more of the primary amine, secondary amine or diamine. Optionally, the amine composition can comprise a tertiary amine in conjunction with the primary and secondary amines.

The alkylated metal or the Grignard reagent can be in liquid form and can be added directly to the intermediate composition. Thus, this invention also provides methods of producing a metal amide comprising combining at least a halogenated transition metal and an amine in a solvent in a container to produce an intermediate composition in the container and adding an alkylated metal or a Grignard reagent to the intermediate composition in the container to produce at least the transition metal amide, wherein the amine composition comprises a primary amine, a secondary amine, or a diamine.

Also provided are methods of producing a metal amide, comprising (a) combining at least a halogenated transition metal and an amine composition in a solvent to produce a first intermediate composition, (b) combining at least (i) a portion of the first intermediate composition and (ii) a portion of an alkylated metal or a Grignard reagent to produce a second intermediate composition, and (c) combining at least (i) a portion of the second intermediate composition and (ii) a portion of the alkylated metal or the Grignard reagent to produce the transition metal amide, wherein the amine composition comprises a primary amine, a secondary amine, or a diamine. Optionally, prior to (b) amine hydrohalide is filtered from the first intermediate composition.

In methods of this invention, the halogenated transition metal can be combined in a stoichiometric amount as to the total amide desired. An excess of amine can be used. For example, when the halogenated transition metal is zirconium chloride, four or more equivalents of methyl ethyl amine can be used to make $Zr(NEtMe)_4$.

In methods of this invention, the intermediate composition or first intermediate composition can comprise a transition metal intermediate.

In particular, such methods are provided wherein the metal amide comprises $M^1(NR^1R^2)_n$, the halogenated transition metal comprises $M^1X^1{}_n$, the amine composition comprises $n(R^1R^2NH)$, the alkylated metal comprises $R^3M^2$, the Grignard reagent comprises $R^4MgX^2$, the intermediate composition comprises a transition metal intermediate $M^1X^1{}_{(n-x)}(NR^1R^2)_x.y(R^1R^2NH)$, wherein n is the valence of $M^1$, x is less than or equal to the maximum oxidation state of $M^1$, and y is from about 0 to about 2. $M^1$ is a transition metal atom, $M^2$ is a non-transition metal atom, each $X^1$ is independently a halogen atom, a cyclopentadienyl, an indenyl, a fluorenyl, an alcohol, a substituted phenol, or the like, provided that at least one $X^1$ is a halogen atom, each $X^2$ is independently a halogen atom, each of $R^1$, $R^2$, and $R^3$ is independently an alkyl having from 1 to about 20 carbon atoms, $R^4$ is independently an alkyl or aryl having from 1 to about 20 carbon atoms, N is nitrogen, H is hydrogen, Mg is magnesium, and n is the valence of $M^1$.

This invention also provides methods of producing a metal amide $M^1(NR^1R^2)_n$ comprising combining at least a halogenated transition metal $M^1X^1{}_n$ and an amine $n(R^1R^2NH)$ in a solvent to produce an intermediate composition comprising $M^1X^1{}_{(n-x)}(NR^1R^2)_x.y(R^1R^2NH)$ and combining at least (i) a portion of the intermediate composition and (ii) an alkylated metal $R^3M^2$ or a Grignard reagent $R^4MgX^2$ in amounts such that the alkylated metal or Grignard reagent is in a stoichiometric amount as to the $M^1X^1{}_{(n-x)}(NR^1R^2)_x.y(R^1R^2NH)$, such as to produce at least the transition metal amide, wherein $M^1$ is a transition metal atom, $M^2$ is a non-transition metal atom, each $X^1$ is independently a halogen atom, a cyclopentadienyl, an indenyl, a fluorenyl, an alcohol, a substituted phenol, or the like, provided that at least one $X^1$ is a halogen atom, each $X^2$ is independently a halogen atom, each of $R^1$, $R^2$, and $R^3$ is independently an alkyl having from 1 to about 20 carbon atoms, $R^4$ is independently an alkyl or aryl having from 1 to about 20 carbon atoms, N is nitrogen, H is hydrogen, Mg is magnesium, and n is the valence of $M^1$.

Also provided are methods of producing a metal amide $M^1(NR^1R^2)_n$ comprising (a) combining at least a halogenated transition metal $M^1X^1{}_n$ and an amine $n(R^1R^2NH)$ in a solvent to produce a first intermediate composition comprising $M^1X^1{}_{(n-x)}(NR^1R^2)_x$. $y(R^1R^2NH)$, (b) combining at least (i) a portion of the first intermediate composition and (ii) a portion of an alkylated metal $R^3M^2$ or a Grignard reagent $R^4MgX^2$ to produce a second intermediate composition, and (c) combining at least (i) a portion of the second intermediate composition and (ii) a portion of the alkylated metal $R^3M^2$ or Grignard reagent $R^4MgX^2$ in amounts such that the alkylated metal or Grignard reagent is in a stoichiometric amount as to the $M^1X^1{}_{(n-x)}(NR^1R^2)_x.y(R^1R^2NH)$, such as to produce at least the transition metal amide, wherein $M^1$ is a transition metal atom, $M^2$ is a non-transition metal atom, each $X^1$ is independently a halogen atom, a cyclopentadienyl, an indenyl, a fluorenyl, an alcohol, a substituted phenol, or the like, provided that at least one $X^1$ is a halogen atom, each $X^2$ is independently a halogen atom, each of $R^1$, $R^2$, and $R^3$ is independently an alkyl having from 1 to about 20 carbon atoms, $R^4$ is independently an alkyl or aryl having from 1 to about 20 carbon atoms, N is nitrogen, H is hydrogen, Mg is magnesium, and n is the valence of $M^1$.

In methods of this invention: transition metal atom $M^1$ can be, e.g., scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubium, seaborgium, bohrium, hassium, meitnerium, ununnilium, unununium, or ununbium; each $X^1$ can independently be a halogen atom, a cyclopentadienyl, an indenyl, a fluorenyl, an alcohol, a substituted phenol, or the like, provided that at least one $X^1$ is a halogen atom; $X^2$ can be, independent from $X^1$, fluorine, chlorine, bromine, or iodine, for example; $R^1$ is independently an alkyl having from 1 to about 20 carbon atoms, for example, methyl or ethyl; $R^2$ is independently an alkyl having from 1 to about 20 carbon atoms, for example, methyl or ethyl; $R^3$ is independently an alkyl having from 1 to about 20 carbon atoms, for example, methyl, ethyl, butyl, or propyl; and $R^4$ is an aryl or an alkyl having from 1 to about 20 carbon atoms. The solvent can be an aprotic hydrocarbon in which the reactants (e.g., transition metals and amines) and reaction products (e.g., intermediate compositions and transition metal amides) are stable. Examples include toluene, benzene, hexanes, isohexane, cyclohexane, methylcyclohexane, ether, tetrahydrofuran (THF), and the like.

In methods of this invention, non-transition metal atom $M^2$ can be any suitable non-transition metal in groups 1 or 2, e.g., lithium, beryllium, sodium, magnesium, etc. Additionally, an amine hydrohalide byproduct can be removed by filtration to reduce the amount of reactant, e.g., $R^3M^2$, needed to convert the transition metal intermediate into the desired metal amide.

EXAMPLES

The following examples are illustrative of the principles of this invention. It is understood that this invention is not limited to any one specific embodiment exemplified herein, whether in the examples or the remainder of this patent application.

Example 1

Preparation of $Hf(NEtMe)_4$ $HfCl_4$ (2.00 g) was slurried in 18.2 g of anhydrous toluene. Ethyl methylamine (1.70 g) was added and a cloudy yellow solution formed. The reaction was then cooled in an ice-water bath and n-BuLi in hexanes was added (2.5M, 10.5 mL). The slurry was allowed to warm to ambient temperature for 3 hours and then heated to 50-55° C. for 3 hours. The white solids were filtered on a medium frit. The volatiles were removed from the yellow filtrate at 5020 C. with vacuum. The isolated yellow oily liquid was determined to be pure $Hf(NMeEt)_4$. The yield was 2.19 g (85%).

Example 2

Preparation of t-BuN═$Ta(NEtMe)_3$ $TaCl_5$ (4.00 g) was slurried in 45.2 g of toluene. A yellow slurry resulted. Ethyl methylamine (2.70 g) was added and a red-orange solution with some crystalline solids formed. After 20 minutes, t-$BuNH_2$ (0.82 g) was added and the reaction mixture changed to yellow over 30 minutes. The reaction was then cooled in an ice-water bath and nBuLi in hexanes were added (2.5M, 22.5 mL). A yellow slurry formed. The slurry was allowed to warm to ambient temperature and to stir overnight. The white solids were filtered on a medium frit. The volatiles were removed from the amber filtrate at 40° C. with vacuum. The t-BuN═$Ta(NEtMe)_3$ was isolated as a viscous amber liquid.

Example 3

Preparation of $Zr(NEtMe)_4$ $ZrCl_4$ (3.59 g) was slurried in 28.2 g of anhydrous toluene. Ethyl methylamine (4.14 g) was added to the $ZrCl_4$ at ambient temperature. A cloudy yellow solution formed. After stirring overnight, the reaction had not changed. The solution was kept under a nitrogen atmosphere and cooled in an ice-water bath. n-BuLi in hexanes was added (2.5M, 23 mL) over 30 minutes. The slurry was allowed to warm to ambient temperature and to stir for 4 hours. An aliquot was removed, diluted with deuterobenzene, and filtered. A $^1H$ NMR showed complete conversion to $Zr(NEtMe)_4$. Dried Celite was added to the reaction (1.52 g) and a roughly equivalent amount was placed on top of a 30 mL coarse frit. A clear orange-yellow filtrate was obtained. The toluene was removed in vacuo. The orange liquid which remained weighed 4.99 g and was determined to be 4.99 g (83%) of $Zr(NMeEt)_4$.

Example 4

Preparation of $Hf(NEtMe)_4$ $HfCl_4$ (2.00 g) was slurried in 17.0 g of anhydrous toluene. Ethyl methylamine (1.7 g) was added and a cloudy yellow solution formed. The reaction was then cooled in an ice-water bath and EtMgCl in diethyl ether was added (2.0M, 12.5 mL). A gelatinous slurry formed. The slurry was allowed to warm to ambient temperature and stirred overnight. The viscous slurry was filtered on a Celite covered frit. The gelatinous solids were washed with 11 g of toluene. The filtrates were combined and analyzed by $^1H$ NMR. Approximately 15% $Hf(NMeEt)_3Cl$ remained. An additional 0.19 g of HNEtMe and then 0.6 mL of EtMgCl solution were added at ambient temperature. After stirring for 4 h, the reaction was analyzed using $^1H$ NMR and the conversion to product was complete. The volatiles were removed and then 5.2 g of toluene was added back to the oily solid. The insoluble material was filtered on a coarse frit. The reddish-orange filtrate weighed 5.49 g and was 16.1 wt % $Hf(NMeEt)_4$ (34% yield).

Example 5

$Ti(NEt_2)_4$

To a cold solution of $HNEt_2$ (29.3 g, 400 mmol) in hexanes (71 g) in an ice/acetone bath was added drop wise a solution of $TiCl_4$ (9.48 g, 50 mmol) in hexane (20 g). The rate of the addition was adjusted so that the temperature of the solution was kept between −2 to 2° C. The addition lasted about 30 minutes and after that the resulting red slurry was allowed to return to room temperature slowly. The slurry was filtered via a medium frit and the white solids ($H_2NEt_2Cl$) was washed with 20 g hexanes. The collected ammonium chloride after drying weighed 11.9 g. The combined filtrate weighed 138 g. According to the weight of the ammonium chloride produced, the weighted empirical formula of the Ti products is calculated to be roughly $Ti(NEt_2)_{2.2}Cl_{1.8}$.

A half of the deep red hexane solution of $Ti(NEt_2)_{2.2}Cl_{1.8}$ from above (69 g, 25 mmol Ti) was cooled in an ice/acetone bath. A 25.4 wt % solution of n-BuLi in hexanes (11.35 g, 45 mmol) was then added. During the addition, which lasted about 20 minutes, the red solution turned into a green slurry gradually. After returning to room temperature, the slurry was allowed to stir overnight. The next day, the slurry was filtered via a medium frit with some filter-aid. The filtered solids were washed with hexanes (~10 ml) until colorless. The combined orange filtrate weighed 63.1 g. The solution was quantitatively analyzed by the 1H NMR which showed the yield of $Ti(NEt_2)_4$ being 68.4%. The solution was then stripped off solvents in vacuo, leaving a deep red oily residue weighing 5.96 g.

Example 6

$Hf(NMe_2)_4$

A light yellow hazy solution of $HfCl_4$ (7.21 g, 22.5 mmol) and $HNMe_2$ (5.80 g, 129 mmol) in THF (20 g) and isohexane (40 g) was cooled in an ice/acetone bath. To this solution was added drop wise a 25.4 wt % of n-BuLi in hexanes (22.7 g, 90 mmol) over a period of 40 minutes. After that the cold bath was removed and the solution was heated in an oil bath to 54° C. for 3 hours. After cooling, the resulting slurry was filtered via a medium frit with some filter-aid and the solids were washed with 10 g of a 2:1 isohexane/THF mixture. The combined filtrate weighed 79.9 g, which was analyzed quantitatively by the 1H NMR showed a 74.4% contained yield of $Hf(NMe_2)_4$. The solvent was stripped off in vacuo and after that the yellow oily residue was vacuum distilled at 70-80° C./2-5 mmHg to give a white solid weighing 5.79 g a 72.5% yield.

Processes according to this invention are particularly advantageous in that they allow for production of transition metal amides in one pot reactions that are equipment and time efficient; don't require expensive ether solvents; don't require slurry transfers (which can be time consuming and lead to reagent stoichiometry problems); and further, the reaction end point can be titrated giving optimum yields (avoids byproducts and waste of expensive alkyl lithium).

It is to be understood that the reactants and components referred to by chemical name or formula anywhere in the specification or claims hereof, whether referred to in the singular or plural, are identified as they exist prior to being combined with or coming into contact with another substance referred to by chemical name or chemical type (e.g., another reactant, a solvent, or etc.). It matters not what chemical changes, transformations and/or reactions, if any, take place in the resulting combination or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a combination to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, combined, blended or mixed with one or more other substances, components and/or ingredients in accordance with the present disclosure. Whatever transformations, if any, which occur in situ as a reaction is conducted is what the claim is intended to cover. Thus the fact that a substance, component or ingredient may have lost its original identity through a chemical reaction or transformation during the course of contacting, combining, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof. As will be familiar to those skilled in the art, the terms "combined", "combining", and the like as used herein mean that the components that are "combined" or that one is "combining" are put into a container with each other. Likewise a "combination" of components means the components having been put together in a container.

While the present invention has been described in terms of one or more preferred embodiments, it is to be understood that other modifications may be made without departing from the scope of the invention, which is set forth in the claims below.

The invention claimed is:

1. A method of producing a metal amide comprising combining at least a halogenated transition metal and an amine composition in a solvent to produce an intermediate composition and combining at least (i) a portion of the intermediate composition and (ii) an alkylated metal or a Grignard reagent to produce at least the transition metal amide, wherein the amine composition comprises a primary amine, a secondary amine, or a diamine.

2. The method of claim 1 wherein the metal amide comprises $M^1(NR^1R^2)_n$, the halogenated transition metal comprises $M^1X^1{}_n$, the amine composition comprises $n(R^1R^2NH)$, the alkylated metal comprises $R^3M^2$, the Grignard reagent comprises $R^4MgX^2$, $M^1$ is a transition metal atom, $M^2$ is a non-transition metal atom, each $X^1$ is independently a halogen atom, a cyclopentadienyl, an indenyl, a fluorenyl, an alcohol, or a substituted phenol, provided that at least one $X^1$ is a halogen atom, each $X^2$ is independently a halogen atom, each of $R^1$, $R^2$, and $R^3$ is independently an alkyl having from 1 to about 20 carbon atoms, $R^4$ is independently an alkyl or aryl having from 1 to about 20 carbon atoms, N is nitrogen, H is hydrogen, Mg is magnesium, and n is the valence of $M^1$.

3. A method of producing a metal amide comprising combining at least a halogenated transition metal and an amine in a solvent in a container to produce an intermediate composition in the container and adding an alkylated metal or a Grignard reagent to the intermediate composition in the container to produce at least the transition metal amide, wherein the amine composition comprises a primary amine, a secondary amine, or a diamine.

4. The method of claim 3 wherein the metal amide comprises $M^1(NR^1R^2)_n$, the halogenated transition metal comprises $M^1X^1{}_n$, the amine composition comprises $n(R^1R^2NH)$, the alkylated metal comprises $R^3M^2$, the Grignard reagent comprises $R^4MgX^2$, $M^1$ is a transition metal atom, $M^2$ is a non-transition metal atom, each $X^1$ is independently a halogen atom, a cyclopentadienyl, an indenyl, a fluorenyl, an alcohol, or a substituted phenol, provided that at least one $X^1$ is a halogen atom, each $X^2$ is independently a halogen atom, each of $R^1$, $R^2$, and $R^3$ is independently an alkyl having from 1 to about 20 carbon atoms, $R^4$ is independently an alkyl or aryl having from 1 to about 20 carbon atoms, N is nitrogen, H is hydrogen, Mg is magnesium, and n is the valence of $M^1$.

5. A method of producing a metal amide, comprising (a) combining at least a halogenated transition metal and an amine composition in a solvent to produce a first intermediate composition, (b) combining at least (i) a portion of the first intermediate composition and (ii) a portion of an alkylated metal or a Grignard reagent to produce a second intermediate composition, and (c) combining at least (i) a portion of the second intermediate composition and (ii) a portion of the alkylated metal or the Grignard reagent to produce the transition metal amide, wherein the amine composition comprises a primary amine, a secondary amine, or a diamine.

6. The method of claim 5 wherein the metal amide comprises $M^1(NR^1R^2)_n$, the halogenated transition metal comprises $M^1X^1{}_n$, the amine composition comprises $n(R^1R^2NH)$, the alkylated metal comprises $R^3M^2$, the Grignard reagent comprises $R^4MgX^2$, $M^1$ is a transition metal atom, $M^2$ is a non-transition metal atom, each $X^1$ is independently a halogen atom, a cyclopentadienyl, an indenyl, a fluorenyl, an alcohol, or a substituted phenol, provided that at least one $X^1$ is a halogen atom, each $X^2$ is independently a halogen atom, each of $R^1$, $R^2$, and $R^3$ is independently an alkyl having from 1 to about 20 carbon atoms, $R^4$ is independently an alkyl or aryl having from 1 to about 20 carbon atoms, N is nitrogen, H is hydrogen, Mg is magnesium, and n is the valence of $M^1$.

7. A method of producing a metal amide $M^1(NR^1R^2)_n$ comprising combining at least a halogenated transition metal $M^1X^1{}_n$ and an amine $n(R^1R^2NH)$ in a solvent to produce an intermediate composition comprising $M^1X^1{}_{(n-x)}(NR^1R^2)_x.y(R^1R^2NH)$ and combining at least (i) a portion of the intermediate composition and (ii) an alkylated metal $R^3M^2$ or a Grignard reagent $R^4MgX^2$ in amounts such that the alkylated metal or Grignard reagent is in a stoichiometric amount as to the $M^1X^1{}_{(n-x)}(NR^1R^2)_x.y(R^1R^2NH)$, such as to produce at least the transition metal amide, wherein $M^1$ is a transition metal atom, $M^2$ is a non-transition metal atom, each $X^1$ is independently a halogen atom, a cyclopentadienyl, an indenyl, a fluorenyl, an alcohol, or a substituted phenol, provided that at least one $X^1$ is a halogen atom, each $X^2$ is independently a halogen atom, each of $R^1$, $R^2$, and $R^3$ is independently an alkyl having from 1 to about 20 carbon atoms, $R^4$ is independently an alkyl or aryl having from 1 to about 20 carbon atoms, N is nitrogen, H is hydrogen, Mg is magnesium, and n is the valence of $M^1$.

8. A method of producing a metal amide $M^1(NR^1R^2)_n$ comprising (a) combining at least a halogenated transition metal $M^1X^1{}_n$ and an amine $n(R^1R^2NH)$ in a solvent to produce a first intermediate composition comprising $M^1X^1{}_{(n-x)}(NR^1R^2)_x.y(R^1R^2NH)$, (b) combining at least (i) a portion of the first intermediate composition and (ii) a portion of an alkylated metal $R^3M^2$ or a Grignard reagent $R^4MgX^2$ to produce a second intermediate composition, and (c) combining at least (i) a portion of the second intermediate composition and (ii) a portion of the alkylated metal $R^3M^2$ or Grignard reagent $R^4MgX^2$ in amounts such that the alkylated metal or Grignard reagent is in a stoichiometric amount as to the $M^1X^1{}_{(n-x)}(NR^1R^2)_x.y(R^1R^2NH)$, such as to produce at least the transition metal amide, wherein $M^1$ is a transition metal atom, $M^2$ is a non-transition metal atom, each $X^1$ is independently a halogen atom, a cyclopentadienyl, an indenyl, a fluorenyl, an alcohol, or a substituted phenol, provided that at least one $X^1$ is a halogen atom, each $X^2$ is independently a halogen atom, each of $R^1$, $R^2$, and $R^3$ is independently an alkyl having from 1 to about 20 carbon atoms, $R^4$ is independently an alkyl or aryl having from 1 to about 20 carbon atoms, N is nitrogen, H is hydrogen, Mg is magnesium, and n is the valence of $M^1$.

* * * * *